United States Patent [19]

Krasner

[11] Patent Number: 4,689,014
[45] Date of Patent: Aug. 25, 1987

[54] METHOD AND APPARATUS FOR PRESERVING AND REIMPLANTING A TOOTH

[76] Inventor: Paul R. Krasner, 285 Maugers Mill Rd., Pottstown, Pa. 19464

[21] Appl. No.: 880,088

[22] Filed: Jun. 30, 1986

[51] Int. Cl.⁴ .............................................. A61C 5/00
[52] U.S. Cl. .................... 433/215; 433/175; 433/229; 206/83; 206/63.5
[58] Field of Search ............... 433/215, 229, 175; 206/63.5, 83, 438

[56] References Cited

U.S. PATENT DOCUMENTS

| | | | |
|---|---|---|---|
| 1,078,431 | 11/1913 | Grier | 206/83 |
| 1,664,419 | 4/1928 | Jackman | 433/77 |
| 2,444,294 | 6/1948 | Jones | 206/83 |
| 2,553,232 | 5/1951 | Beyer | 206/63.5 |
| 2,699,780 | 1/1955 | Rudnick et al. | 206/63.5 |
| 2,711,021 | 6/1955 | Parker | 433/175 |
| 2,973,767 | 3/1961 | Cohen | 206/83 |
| 3,337,042 | 8/1967 | Bergendal et al. | 206/63.5 |
| 3,337,957 | 8/1967 | Reed | 433/215 |
| 3,360,122 | 12/1967 | Ruckert | 206/63.5 |
| 3,765,564 | 10/1973 | Persson | 433/25 |
| 3,874,082 | 4/1975 | Stein | 433/228.1 |
| 4,172,128 | 10/1979 | Thiele et al. | 433/173 |
| 4,203,217 | 5/1980 | Kurer | 433/220 |
| 4,360,342 | 11/1982 | Salvo | 433/225 |
| 4,443,197 | 4/1984 | Fusayama | 433/217 |
| 4,494,652 | 1/1985 | Nelson et al. | 206/63.5 |

OTHER PUBLICATIONS

"Milk and Saliva as Possible Storage Media . . . ", Leif Blomlöf, Swedish Dental Journal, vol. 5, Supp. No. 8, pp. 1-26 (1981).

"Periodontal and Pulpal Healing of Monkey Incisors . . . ", J. O. Andreasen et al., Int. J. Oral Surgery, vol. 7, pp. 104-112 (1978).

"Effect of Storage in Media with Different Ion Strengths . . . ", L. Blomlöf et al., vol. 89, pp. 180-187 (1981).

Primary Examiner—John J. Wilson
Attorney, Agent, or Firm—William H. Eilberg

[57] ABSTRACT

A method and apparatus are disclosed for saving an exarticulated tooth. The tooth is grasped by its crown, so as not to harm the periodontal membrane. The tooth is then placed in a net which is attached to a basket. The net and basket are immersed in a modified saline solution which preserves the cells of the periodontal membrane. The solution is held in a container which accommodates the net and basket. The lid of the container has a sponge attached to its interior surface. The container is closed, and the tooth and patient are taken to a dentist. The dentist removes the container lid, and lays the lid on a table or other surface, so that the sponge faces upward. The dentist then lifts the basket, with the tooth, out of the solution, and inverts the net so that the tooth falls out onto the sponge. The dentist grasps the tooth with a forceps and reimplants it in the patient's mouth.

21 Claims, 5 Drawing Figures

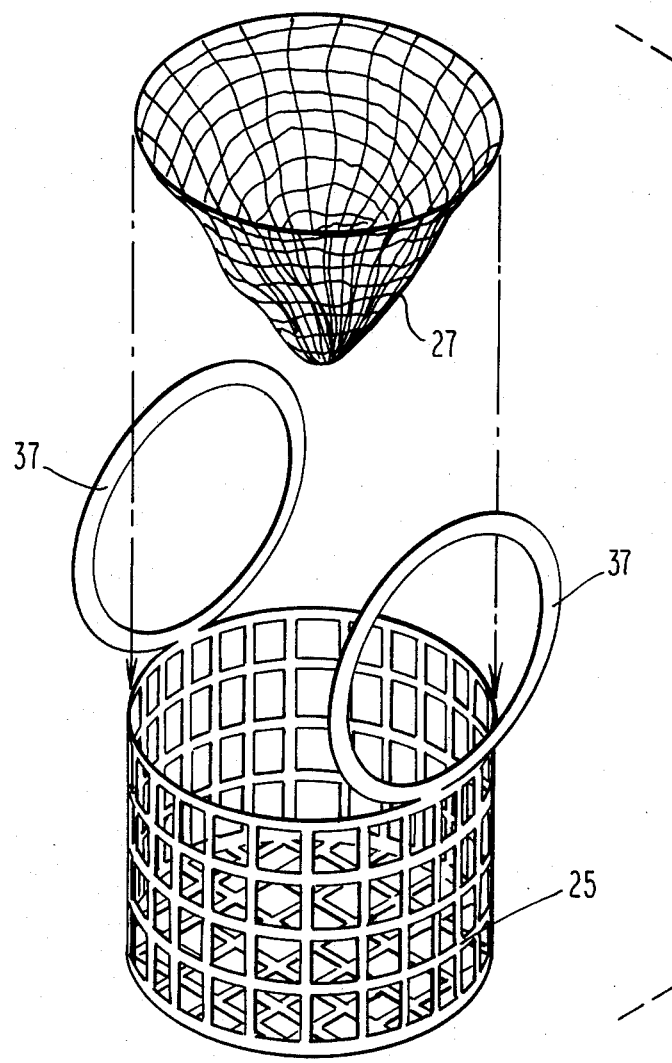
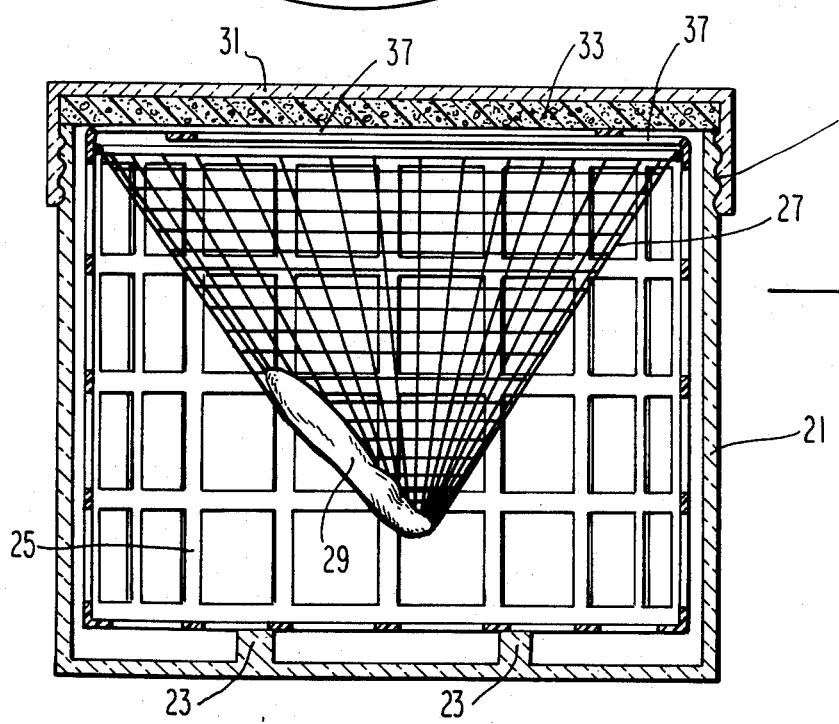

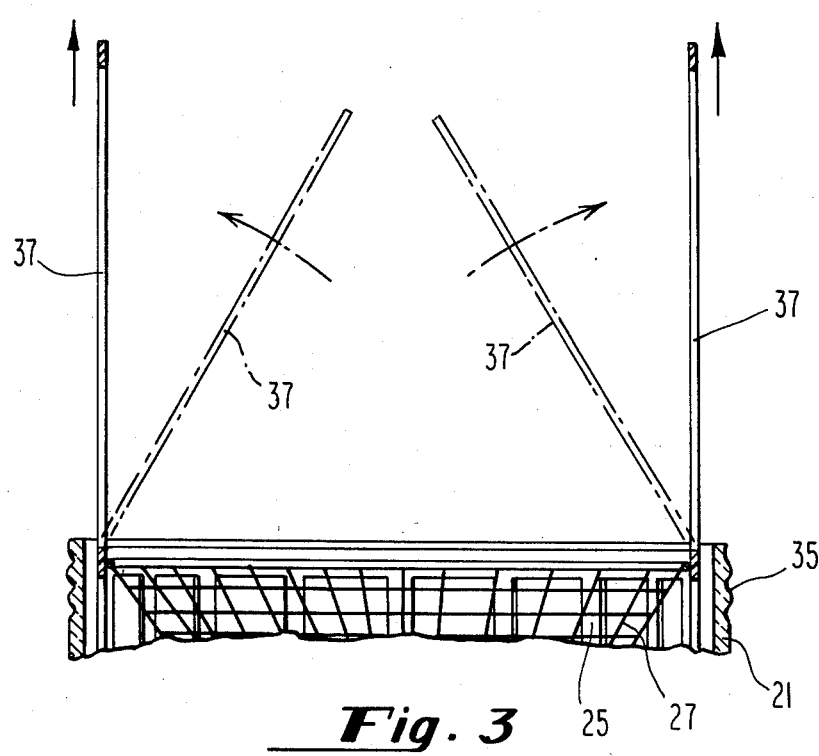
Fig. 3
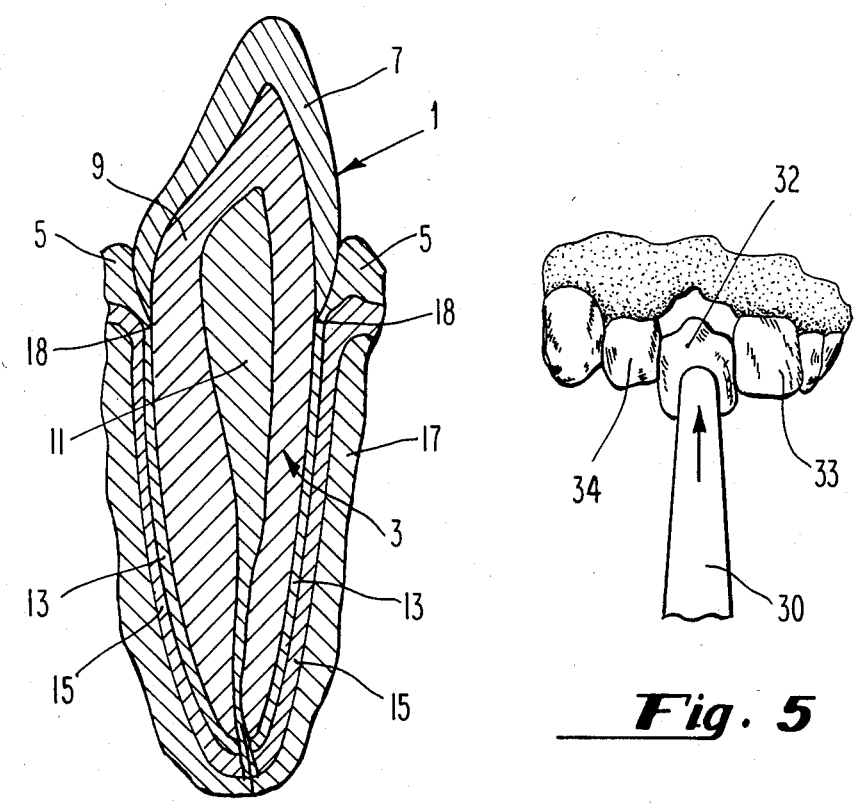
Fig. 4
Fig. 5

METHOD AND APPARATUS FOR PRESERVING AND REIMPLANTING A TOOTH

BACKGROUND OF THE INVENTION

This invention discloses a method and related apparatus for saving a tooth which has been exarticulated, or knocked out.

Exarticulation of a tooth, also known as an avulsion, occurs when the entire tooth is forcefully and completely knocked out of its socket. Tooth exarticulation is quite common, especially among children. Exarticulation can result from falls, violence, or other causes. It is possible to save an exarticulated tooth, but only if the proper procedures are followed. Due to public ignorance, these procedures are seldom followed. When the exarticulated tooth is brought to a dentist, it is often too late to save the tooth.

All teeth have two main components, namely the crown and the root. The crown is the portion of the tooth that protrudes from the gum, and is normally the only visible part of the tooth. The root is the portion of the tooth embedded in the gum. The entire tooth root is surrounded by the periodontal membrane, also known as the periodontal ligament. The periodontal membrane is a soft, ligamentous material which connects the tooth to its bony socket. The periodontal membrane surrounds the entire root, but does not extend onto the crown.

If the periodontal membrane of an exarticulated tooth has not been substantially damaged, and if its cells are still alive, the tooth can be successfully reimplanted in its socket. After several days, the tooth will become naturally reaffixed to the socket. But if the cells of the membrane have died, the tooth is lost.

It has been known that, if an exarticulated tooth is stored in a proper medium, its periodontal membrane can be preserved, and the tooth can be saved. Various experiments have been done to determine which media are best for storing an exarticulated tooth. One article describing such experiments is "Milk and Saliva as Possible Storage Media for Traumatically Exarticulated Teeth Prior to Replantation", by L. Blomlof, Swedish Dental Journal, vol. 5, Supp. No. 8, pages 1-26 (1981). As indicated by the title, the article describes experiments which tested the effectiveness of milk and saliva as storage media for exarticulated monkey teeth. Both of these naturally-occurring media were found to be effective in promoting the vitality of the cells of the periodontal membrane.

The above-cited article also reports the results of experiments with artificial storage media. The medium that performed best in most of the experiments is the solution known as "Eagle's medium". Eagle's medium was first described in the article by M. Eagle, entitled "Amino acid metabolism in mammalian cell cultures", in *Science,* vol. 130, pages 432–437 (1959). Eagle's medium has been modified by others, and is available commercially from various sources.

The other artificial medium which has been shown effective in preserving an exarticulated tooth is the Hanks Balanced Salt Solution. This solution was also used successfully in the experiments reported in the above-cited article.

Other experiments on the preservation of monkey teeth in Eagle's medium have been reported in "Periodontal and Pulpal Healing of Monkey Incisors Preserved in Tissue Culture Before Replantation", by J. O. Andreasen et al, in the International Journal of Oral Surgery, vol. 7, pages 104–112 (1978). And the Hanks solution has been further tested, and found to be effective, in experiments reported in the article by L. Blomlof et al, entitled "Effect of Storage in Media with Different Ion Strength and Osmolalities on Human Periodontal Ligament Cells", in the Scandinavian Journal of Dental Research, vol. 89, pages 180–7 (1981).

In theory, it is thus comparatively easy to preserve an exarticulated tooth, and then to reimplant it. Unfortunately, exarticulation of a tooth is a traumatic experience for the victim. If the victim is a child, the trauma can be equally severe for the parent as well. Neither parents nor children are usually well-informed about how to preserve a tooth in this kind of emergency. Very often, by the time the tooth has been carried to a dentist, the cells of the periodontal membrane have died, and it is too late to save the tooth.

The present invention provides a simple method for saving an exarticulated tooth, and also provides an apparatus which is especially useful in practicing the method. The invention makes it possible for the general public to apply the above-described scientific findings for practical benefit.

SUMMARY OF THE INVENTION

According to the invention, an exarticulated tooth is picked up by its crown, so as not to harm the periodontal membrane. The tooth is then dropped into a net, the net being attached to a rigid, or semi-rigid, basket. The basket rests in a container of a modified saline solution which tends to enhance the vitality of the cells of the periodontal membrane.

The lid of the container has a sponge means on its interior surface. The lid is screwed onto the container, and the tooth and patient are transported to the nearest dentist. The dentist opens the container, and places the lid on a working surface, so that the sponge means faces upward. The dentist then lifts the basket, with the net, from the solution, and inverts the net so that the tooth falls out onto the sponge means. The tooth is then gripped with a forceps, or other suitable tool, and reimplanted into its socket.

The basket can be constructed of metal or plastic, and is preferably equipped with a pair of handles which facilitate the lifting of the basket out of the solution. The solution is preferably a modified saline solution, such as a Hanks' Balanced Salt Solution or an Eagle's medium.

It is therefore an object to provide a method for saving an exarticulated tooth.

It is another object of the invention to provide a method for storing the exarticulated tooth, and transporting it to a dentist.

It is another object of the invention to provide apparatus which facilitates the practice of the method described above.

It is another object to provide a basket and net structure which is especially adapted for use in storing and transporting an exarticulated tooth.

It is another object to provide apparatus which can be used with commercially available media for storing and transporting exarticulated teeth.

Other objects and advantages of the invention will be apparent to those skilled in the art, from a reading of the following brief description of the drawings, the detailed description of the invention, and the appended claims.

BRIEF DESCRIPTION OF THE DRAWINGS

FIG. 1 is a cross-sectional view of the container for storing a tooth, having a basket and net, constructed according to the present invention.

FIG. 2 is an exploded perspective view showing both the basket, and the net attached to the basket.

FIG. 3 is a fragmentary cross-sectional view, showing the structure of the handles by which the basket can be lifted from the container.

FIG. 4 is a diagram of the components of a tooth.

FIG. 5 is a diagram illustrating the reimplantation of a tooth into a patient's mouth.

DETAILED DESCRIPTION OF THE INVENTION

The present invention provides a simple method and apparatus for saving a tooth that has been exarticulated, or suddenly and completely knocked out of the patient's mouth.

In order to understand the invention, it is helpful to review the anatomy of a tooth. FIG. 4 is a diagram showing, in cross-section, the principal components of a single-rooted tooth. The tooth has a crown portion, designated generally by reference numeral 1, and a root portion, designated generally by reference numeral 3. The crown is the portion of the tooth which protrudes from the gingiva (or gum) 5.

The crown portion has a coating of enamel 7, under which is located a layer of dentin 9, a tubular structure which supports the enamel and provides a sensory mechanism. Pulp chamber 11 contains the nerve of the tooth. The outer covering of the root of the tooth is known as the cementum, and is designated by reference numeral 13. The periodontal membrane 15, also known as the periodontal ligament or PDL, is disposed between the cementum 13 and the bony socket 17 in which the tooth rests.

The location at which the enamel 7 abuts the cementum 13 is known as the cemento-enamel junction, and is designated by reference numeral 18. Roughly speaking, the cemento-enamel junction is the portion of the tooth where the tooth crown meets the tooth root.

The tooth shown in FIG. 4 is a single-rooted tooth. Other teeth, such as molars, have two roots, which are connected to each other. The structure of single-rooted and double-rooted teeth is otherwise the same as shown in FIG. 4.

When a tooth is exarticulated, or knocked out, the periodontal membrane generally remains with the tooth. If this membrane is undamaged, it is possible to reimplant the tooth in its socket, and, after a few days, the tooth will become firmly and naturally reattached.

The present invention includes an apparatus, illustrated in FIGS. 1–3, for facilitating the storage and transportation of an exarticulated tooth. The device comprises container 21, which can be a jar or bottle. Disposed within container 21 is basket 25 which rests on feet 23. Feet 23 can be integrally formed with the container, as shown, or they can be made part of the basket. The basket can be of wire mesh construction, or can be formed of plastic. Attached to basket 25 is net 27, which can be made of nylon, or other flexible material. The size of the net is such that it encloses a volume less than that of the container. FIG. 1 shows tooth 29 resting within net 27. For the sake of clarity, no fluid is shown in the container, in FIG. 1, but it is understood that, when the container is used to store a tooth, the interior of the container will be filled with a solution which tends to promote the vitality of the cells of the periodontal membrane.

Container 21 is closed off with lid 31. Mounted on the interior surface of lid 31 is sponge 33. The "interior surface" means the surface which is inside the container when the lid is attached to the container. The sponge helps to seal the contents of the container, although this seal need not be especially tight. The sponge has a more specific function, in the invention, as will be described below. Lid 31 is screwed onto the container, by threads 35.

A pair of handles 37, more plainly visible in the exploded perspective view of FIG. 2, are attached to the basket 25. The handles are used to lift the basket from the container. The handles shown in the figures are of the form of generally circular rings, and are pivotably attached to the periphery of the basket. The rings can be folded over each other while the lid is screwed onto the container. FIG. 1 shows handles 37 in this fully folded-down position. The view of FIG. 3 shows the movement of handles 37, as they are being opened, so as to lift the basket.

The method of the present invention can now be described. First, the exarticulated tooth is picked up from the ground. In grasping the tooth, it is important to touch only the crown portion (reference numeral 7 in FIG. 4), and not the periodontal membrane 15.

Lid 31 of container 21 is then unscrewed. The container is filled with a modified saline solution, as described below. It is possible to store the solution separately from the container, and to pour the solution into the container when needed. It may be more convenient to store the solution permanently in the container.

The tooth is dropped into the net, and into the solution. The container lid is reaffixed to the container. The container and the patient are then brought to a dentist as quickly as possible. The tooth remains gently suspended in the solution. Because the volume of the net is smaller than that of the basket, the tooth is unlikely to collide with the walls of the basket during transportation.

When the patient arrives at the dentist's office, with the container and the tooth, the dentist unscrews the lid, and places it on a flat working surface, so that the sponge faces upward. The dentist then lifts the basket, by its handles, out of the container and the solution. The basket, with the net still attached, is then gently inverted, so that the tooth falls out onto the sponge. The dentist takes a tooth extraction forceps, as illustrated by reference numeral 30 in FIG. 5, or any other equivalent implement, and gently grips the tooth 32 by its crown portion so that the tips of the forceps extend no further than the level of the cemento-enamel junction, with the apex of the root facing away from the forceps. The dentist carries the tooth, in the forceps, to the patient, who has been anesthetized, and reimplants the tooth in its socket.

FIG. 5 shows the tooth 32 being reimplanted, between teeth 33 and 34, by forceps 30. If the periodontal membrane has not been damaged during storage and transportation, it will reattach itself naturally to the socket in about 2–3 days, and the healing process is usually complete in about two weeks.

In practice, one needs a retaining means (not shown in the drawings) for holding the reimplanted tooth in place. There are many well-known ways of retaining the tooth. One way is to attach brackets to the teeth, which hold the reimplanted tooth while allowing the tooth some movement. Another method is to use a bonding material, of the type commonly used to fill chipped teeth and the like, to connect the reimplanted tooth to its neighbors. The bonding material allows the tooth to move somewhat. After the healing process is complete, the bonding material can be removed.

The only unacceptable means of retaining the reimplanted tooth is the use of a rigid bar which prevents any movement of the reimplanted tooth. Such a rigid retaining means can cause ankylosis, a condition in which the bone around the tooth becomes connected directly to the dentin, and the periodontal membrane is entirely lost.

As stated above, two preferred solutions for use in the container are the so-called Hanks' Balanced Salt Solutions, and Eagle's medium. Both of these media are are commercially available from Gibco Laboratories, of Grand Island, N.Y., and from other sources.

The Hanks solutions contain a mixture of various inorganic salts, plus certain other components. The salts found in several variations of the Hanks solutions are shown in the following table.

| | Concentration in g/l | | | | |
|---|---|---|---|---|---|
| | Solution No.: | | | | |
| Component: | 1 | 2 | 3 | 4 | 5 |
| $CaCl_2$ (anhyd.) | 0.14 | 0 | 1.40 | 0 | 0.14 |
| KCl | 0.40 | 0.40 | 4.00 | 4.00 | 0.40 |
| $KH_2PO_4$ | 0.06 | 0.06 | 0.60 | 0.60 | 0.06 |
| $MgCl_2 \cdot 6H_2O$ | 0.10 | 0 | 1.00 | 0 | 0 |
| $MgSO_4$ (anhyd.) | 0 | 0 | 0 | 0 | 0.0977 |
| $MgSO_4 \cdot 7H_2O$ | 0.10 | 0 | 1.00 | 0 | 0 |
| NaCl | 8.00 | 8.00 | 80.00 | 80.00 | 8.00 |
| $NaHCO_3$ | 0.35 | 0.35 | 0 | 0 | 0 |
| $Na_2HPO_4$ | 0 | 0 | 0 | 0 | 0.048 |
| $Na_2HPO_4 \cdot 7H_2O$ | 0.09 | 0.09 | 0.90 | 0.90 | 0 |

The Hanks solutions also contain a certain amount of glucose, for purposes of providing nutrition for the cells stored in the solution, and may also contain a coloring agent.

Solutions Nos. 3 and 4 can be characterized as more concentrated versions of Solutions Nos. 1 and 2.

Eagle's medium, in its modified forms, includes inorganic salts of the types shown in the above table, plus vitamins, amino acids, and antibiotics. More specifically, the amino acids which are used in the Eagle's medium available from Gibco Laboratories include L-Arginine, L-Cystine, L-Glutamine, L-Histidine, L-Isoleucine, L-Leucine, L-Lysine, L-Methionine, L-Phenylalanine, L-Threonine, L-Tryptophane, L-Tryosine, and L-Valine. The vitamins used in the Eagle's medium sold by Gibco include biotin, D-Ca pantothenate, choline chloride, folic acid, I-inositol, nicotinamide, pyridoxal HCl, riboflavin, and thiamine HCl. In the experiments reported in the article by Blomlof in the Swedish Dental Journal, cited above, the Eagle's medium was augmented by calf serum.

A major purpose of the Hanks solution, or Eagle's medium, or any other type of artificial solution used to store a tooth, is to provide a composition which most nearly duplicates that of the fluid in the cells being preserved. If the tooth is stored in a solution which does not match the composition of the cell contents, there will be a net inflow or outflow of ions across the boundary of the cell. This ion transport can destroy the cell. In fact, if the tooth is placed in pure water, the difference in ion concentration between the interior and exterior of the outer cells on the periodontal membrane will cause those cells to explode, thereby killing them.

Because water can kill the cells of the periodontal membrane, it is not recommended that the tooth be rinsed with water before reimplantation. Moreover, the tooth will be rinsed automatically when it is stored and transported in one of the solutions described above.

The Hanks solutions and Eagle's medium have been shown to be particularly effective in preserving the vitality of the cells of the periodontal membrane. Indeed, the experiments with Eagle's medium suggest that it is possible to store exarticulated teeth in that medium for several days without damage to the membrane. The Hanks solution appears to be effective for several hours, but it may have the advantage of having a longer shelf life than Eagle's medium.

It is quite possible that other artificial solutions can be used as well. There are many other such solutions, which are commercially available, and which have been developed for use by research laboratories for the purpose of preservation of various natural tissues. Examples include the so-called Gey's Balanced Salt Solution and Puck's Saline. However, the latter solutions are not believed to have been tested with exarticulated teeth.

The specific embodiment described above should be considered exemplary, and not limiting. The invention can be modified in many ways, within the scope of the disclosure. For example, the structure of the container can be varied, and the basket and net can assume different forms. Different types of sponge materials, and different types of closures for the container, can be employed. The basket can be made without handles, or the handles can be formed in other shapes. As described above, various balanced solutions could be used to preserve the tooth. Both the Hanks solutions and Eagle's medium represent entire families of solutions, and it is possible that other cellpreserving solutions could be substituted. These and other similar modification should be considered within the spirit and scope of the following claims.

What is claimed is:

1. A method of preserving and reimplanting an exarticulated tooth into a patient's mouth, comprising the steps of:
    (a) picking the tooth up by its crown,
    (b) dropping the tooth into a flexible net, the net being attached to a basket and being suspended from the basket, the net and basket being disposed in a container substantially filled with an inorganic salt solution, the container being sealable by a lid having a sponge means attached to its interior surface,
    (c) transporting the continer and patient to a location where dental aid is available,
    (d) removing the lid from the container, and laying the lid on a flat surface, such that the sponge means faces upward,
    (e) lifting the basket and net out of the solution,
    (f) turning the basket over, so that the tooth comes to rest on the sponge means,
    (g) grasping the crown of the tooth with a forceps, without touching the periodontal membrane of the tooth, and
    (h) reimplanting the tooth into the mouth of the patient.

2. The method of claim 1, wherein the transporting step is preceded by the step of attaching the lid to the container, so that the tooth is substantially sealed within the container.

3. The method of claim 2, wherein the attaching step comprises screwing the lid onto the container.

4. The method of claim 1, wherein the basket has at least one handle means, and wherein the lifting step comprises the step of pulling the basket, by the handle means, out of the container, and out of the solution.

5. A method of preserving an exarticulated tooth, comprising the steps of:
   (a) placing the tooth in a net, the net being immersed in a solution,
   (b) storing the tooth in the net, in the solution, until dental aid is available,
   (c) lifting the net from the solution,
   (d) removing the tooth from the net, and
   (e) reimplanting the tooth.

6. The method of claim 5, wherein the placing step includes the step of grasping the tooth by its crown.

7. The method of claim 6, wherein the net is attached to a substantially rigid basket, the basket being disposed within a container.

8. The method of claim 7, wherein the container includes a lid having a sponge means disposed along its interior surface.

9. The method of claim 8, wherein the lifting step comprises the step of lifting the basket from the container.

10. The method of claim 9, wherein the removing step comprises the steps of laying the lid of the container so that the sponge means faces upward, and inverting the the net so that the tooth falls out onto the sponge means.

11. Apparatus for preserving an exarticulated tooth, comprising:
   (a) a container means, the container means having a lid which is attachable to the container means, the lid having an interior surface, the lid having a sponge means attached to its interior surface,
   (b) a basket means, the basket means being capable of being inserted into the container means, and
   (c) a net means, the net means being attached to the basket means, the net means having a mesh size sufficient to hold the tooth in the net means.

12. The apparatus of claim 11, wherein the basket includes feet which are adapted to rest on the bottom of the container means.

13. The apparatus of claim 11, wherein the basket means includes at least one handle means, wherein the basket means and the net means can be lifted out of the container means by lifting the handle means.

14. The apparatus of claim 13, wherein the handle means comprises a ring, the ring being pivotably attached to the basket means, the ring being adapted to rest generally around the periphery of the basket means.

15. The apparatus of claim 14, wherein there are a pair of rings, the rings being attached to the basket means at distinct locations on the periphery of the basket means.

16. A kit for preserving a tooth, comprising:
   (a) a container,
   (b) a lid adapted to be affixed to the container, the lid having a sponge means attached to its interior surface,
   (c) a basket, the basket being capable of being placed within the container, the basket having at least one opening through which a fluid can flow,
   (d) a net attached to the basket, and
   (e) a solution suitable for preserving a tooth.

17. The kit of claim 16, wherein the basket includes at least one handle, attached to the basket.

18. The kit of claim 17, wherein there are a pair of handles, the handles comprising rings which are pivotably attached to the basket, wherein the rings are foldable over each other, within the container, when the lid is affixed.

19. The kit of claim 18, wherein the net has a size which encloses a volume less than that of the container.

20. The kit of claim 19, wherein the solution contains a plurality of inorganic salts.

21. The kit of claim 20, wherein the solution contains amino acids and antibiotics.

* * * * *